United States Patent [19]

Mortensen

[11] Patent Number: 4,610,656
[45] Date of Patent: Sep. 9, 1986

[54] FULLY PORTABLE SEMI-AUTOMATIC MECHANICAL HEART-LUNG SUBSTITUTION SYSTEM AND METHOD

[75] Inventor: J. D. Mortensen, Salt Lake City, Utah

[73] Assignee: Mehealus Partnership, Sandy, Utah

[21] Appl. No.: 642,833

[22] Filed: Aug. 21, 1984

[51] Int. Cl.$^4$ .......................................... A61M 37/00
[52] U.S. Cl. ................................. 604/4; 128/DIG. 3
[58] Field of Search ...................... 604/4, 5, 6, 50, 67; 128/DIG. 3, 675; 422/45, 46, 47, 48; 417/540, 542

[56] References Cited

U.S. PATENT DOCUMENTS

| | | | |
|---|---|---|---|
| 3,437,450 | 4/1969 | Greenwood | 422/46 |
| 3,506,406 | 4/1970 | Birch, Jr. | 422/48 |
| 3,513,845 | 5/1970 | Chesnut et al. | 604/4 |
| 3,890,969 | 6/1975 | Fischel | 604/4 |
| 3,903,895 | 9/1975 | Alley et al. | 128/DIG. 3 |
| 3,907,504 | 9/1975 | Hammond et al. | 422/46 |
| 3,927,980 | 12/1975 | Leonard | 422/48 |
| 4,248,224 | 2/1981 | Jones | 128/675 |
| 4,297,890 | 11/1981 | Hok | 128/675 |
| 4,540,399 | 9/1985 | Litzie et al. | 604/4 |

OTHER PUBLICATIONS

Glaviano et al, American Journal of Physiology, vol. 197, No. 1, Jul. 1959.
Dennis et al., "Clinical Use of a Cannula for Left Heart Bypass without Thoracotomy: Experimental Protection Against Fibrillation by Left Heart Bypass," Annals of Surg. 156:623, (1962).
Bodell et al., "A Capillary Membrane Oxygenator," G. Thoracic and Cardiovas. Surg., 46:639, (1963).
Bodell et al., "An Implantable Artificial Lung," JAMA, 191:125, (1965).
Dorson et al., "A Long-Term Partial Bypass Oxygenation System," Annals of Thoracic Surg., 8:296, (1969).
LaFarge et al., "The Maintenance of Circulatory Competence During Chronic Microsphere-Induced Myocardial Failure," J. Thoracic and Cardiovas. Surg., 62:652, (1972).
Turina et al., "Servo-Controlled Extended Cardiopulmonary Bypass," Trans. ASAIO, 19:504, (1973).
Gille et al., "Ten Years of Use of Extracorporeal Membrane Oxygenation (ECMO) in the Treatment of Acute Respiratory Insufficiency (ARI), " Trans. ASAIO, 22:102, (1976).
Landé et al., "Mobile Profound Life Support," Trans. ASAIO, 23:736, (1979).

(List continued on next page.)

Primary Examiner—Richard C. Pinkham
Assistant Examiner—Benjamin Layno
Attorney, Agent, or Firm—Workman, Nydegger & Jensen

[57] ABSTRACT

A fully portable, semi-automatic mechanical heart-lung substitution system and method. The system includes a venous cannula adapted for insertion into the vena cava of the patient and an arterial cannula adapted for insertion into the right and/or left common carotid artery of the patient. The venous cannula is attached to a roller pump used to pump blood from the patient's right heart to a membrane oxygenator. The speed of the roller pump is automatically controlled by means of a pressure sensor that is attached to the outer wall of the venous cannula so as to sense the internal venous blood pressure inside the patient's vena cava. Blood flows from the oxygenator to a compliance reservoir which expands so as to create increasing pressure within the reservoir as the volume of blood filling the reservoir increases. Blood pressure within the compliance reservoir serves as the filling pressure for a pulsatile left heart pump such that the stroke volume of the left heart pump is automatically controlled so that the volume and rate of oxygenated blood returned to the patient is substantially the same as the volume and rate of venous blood pumped out of the patient. Oxygenated blood is returned to the patient's arterial system through the arterial cannula. The entire system then filtered and can be transported by hand for use outside the environment of a hospital facility.

67 Claims, 5 Drawing Figures

OTHER PUBLICATIONS

Bartlett et al., "Extracorporeal Membrane Oxygenation (ECMO) in the Treatment of Cardiac and Respiratory Failure in Children," Trans. ASAIO, 26:578, (1980).

Bodnar et al., "Emergency Left Heart Bypass," Proceedings of the Second Meeting of ISAO, (1979).

Philippe et al., "Automated Microprocessor Controlled Combined Cardiac Assist in Profound Biventricular Failure," Trans. ASAIO, 26:432, (1980).

Mohrman, "Special Communications: A Servo-Controlled Roller Pump for Cardiovascular Research", American Physiological Society, (1980).

Vered et al., "A Second Generation Portable Life Support System," Trans. ASAIO, 26:39, (1980).

MacDonnell et al., "Extracorporeal Membrane Oxygenator Support in a Case of Severe Status Asthmaticus," Annals of Thoracic Surgery, 31:171, (1981).

Phillips et al., "Percutaneous Initiation of Cardiopulmonary Bypass," Annals of Thoracic Surg., 36:223, (1983).

Bedell et al., "Survival After Cardiopulmonary Resuscitation in the Hospital," New England, J. Med., 309:569, (1983).

Phillips et al., "Percutaneous Initiation of Cardiopulmonary Bypass," Annals of Thoracic Surg., 36:223, (1983).

FULLY PORTABLE SEMI-AUTOMATIC MECHANICAL HEART-LUNG SUBSTITUTION SYSTEM AND METHOD

BACKGROUND

1. Field of the Invention

The present invention relates to systems and methods for cardiopulmonary bypass, and in particular the present invention relates to a novel system and method of mechanical heart-lung substitution which is fully portable and semi-automatic and which is particularly adapted for utilization outside the hospital environment as an emergency life-support system for sustaining the life of a patient suffering from acute, severe, lift-threatening cardiac and/or respiratory failure.

2. The Prior Art

When acute, severe, life-threatening but potentially reversible interruption of natural cardiac and/or pulmonary function occurs, emergency application of effective methods for maintaining at least partial cardiopulmonary function until the primary threat to life can be corrected may permit all vital organs and/or systems to resume normal self-regulating function, thereby averting death. In actual clinical practice, such life-support efforts currently take one of three forms: (1) emergency cardiopulmonary resuscitation (CPR); (2) temporary mechanical cardiopulmonary bypass (CPB) for support of patients undergoing open heart surgery; and (3) modified partial cardiopulmonary bypass, which is also called extracorporeal membrane oxygenation (ECMO), which is used for mechanical assistance of patients in acute, severe but reversible pulmonary failure.

CPR is used each day to save literally several hundred persons who collapse unexpectedly at home, at work, in the field, or in hospitals, and is an accepted technique for providing temporary cardiopulmonary assistance in emergency situations. However, there is no question that cardiopulmonary bypass machines or extracorporeal membrane oxygenation systems are much more effective in maintaining proper hemodynamic function and blood gas exchanges than is cardiopulmonary resuscitation. In proper hospital environments, cardiopulmonary bypass and/or extracorporeal membrane oxygenation can be carried out longer and with much higher survival rates than can be achieved with cardiopulmonary resuscitation.

Unfortunately, notwithstanding the substantial advantages that can be derived from using cardiopulmonary bypass and/or extracorporeal membrane oxygenation systems, such systems are not currently available outside the operating room or hospital environment, and they require considerable preparation time before they can be applied. For example, typical cardiopulmonary bypass machines are relatively large in size and are highly complicated, usually requiring the use of skilled perfusionists in order to run them. Patients who undergo cardiopulmonary bypass also require major thoracic surgery and therefore the presence of a skilled surgeon is needed in typical situations. Moreover, proper management of the usual cardiopulmonary bypass machine requires the use of highly technical invasive monitoring systems to monitor and record the vital signs of the patient. Thus, for obvious reasons, these types of cardiopulmonary bypass and/or extracorporeal membrane oxygenation systems are not available or practical for use outside the setting of a rather sophisticated hospital facility.

It would be a substantial advance in the state of the art to provide a fully portable mechanical heart-lung substitution system which could be used without the need for major surgical operation and which would be semi-automatic so as to simplify the ease of using and the reliability of such a system. Such an invention would have an important impact on the ability of paramedics or other emergency personnel to provide adequate, temporary cardiopulmonary life support while transporting a patient to a fully equipped hospital facility for longer term or more definitive care. Such an invention is disclosed and claimed herein.

BRIEF SUMMARY AND OBJECTS OF THE INVENTION

The present invention comprises a fully portable, semi-automatic mechanical heart-lung substitution system and method. In one presently preferred embodiment of the invention, the system includes a venous cannula that is adapted for insertion under local anaesthetic through the vena caval system of the patient beginning at the right internal jugular vein and continuing to a point inside the right ventricle of the heart. The venous cannula is attached to a roller pump which is used to pump blood from the patient's right heart to a membrane oxygenator connected at the output of the roller pump. The speed of the roller pump is automatically controlled by means of a pressure sensor that is attached to the outer wall of the venous cannula so as to sense the internal venous blood pressure inside the patient's vena cava.

From the oxygenator, the blood flows to a compliance reservoir which expands so as to created increasing pressure as the volume of the blood filling the reservoir increases. The compliance reservoir is connected to a pulsatile left heart pump, and the stroke volume of the left heart pump is automatically controlled by the pressure developed in the compliance reservoir. Blood is output by the pulsatile left heart pump through a filter and bubble trap and then is returned to the patient's arterial system through an arterial cannula that is inserted under local anaesthetic into the right and/or left common carotid artery. The entire system is mounted on a small carrying case which can be transported by hand by emergency personnel.

It is therefore a primary object of the present invention to provide a fully portable semi-automatic mechanical heart-lung substitution system and method which can be employed by emergency personnel in the field for purposes of providing life sustaining cardiopulmonary function in a safe and reliable manner.

Another important object of the present invention is to provide a portable self-contained mechanical heart-lung substitution system which can be applied and discontinued without general anaesthesia and without major surgery.

Yet another important object of the present invention is to provide a mechanical heart-lung substitution system which minimizes the need for systemic anticoagulation of the patient so as to minimize the potential for hemorrhage in the case of seriously injured patients.

Still another important object of the present invention is to provide a system and method of heart-lung substitution which does not require invasive monitoring.

Another important object of the present invention is to provide a system and method of heart-lung substitution which is semi-automatic so as to provide effective and reliable life support of cardiopulmonary function without the need for constant attendance of skilled perfusionists or other technicians.

Yet another important object of the present invention is to provide a system and method of heart-lung substitution which can be maintained in a fully portable, sterile, primed and ready to apply condition for emergency use and which can be instituted and become operational within a matter of minutes.

These and other objects and features of the present invention will become more fully apparent from the following description and appended claims taken in conjunction with the accompanying drawings.

DETAILED DESCRIPTION OF THE PRESENTLY PREFERRED EMBODIMENT

Figure 1:
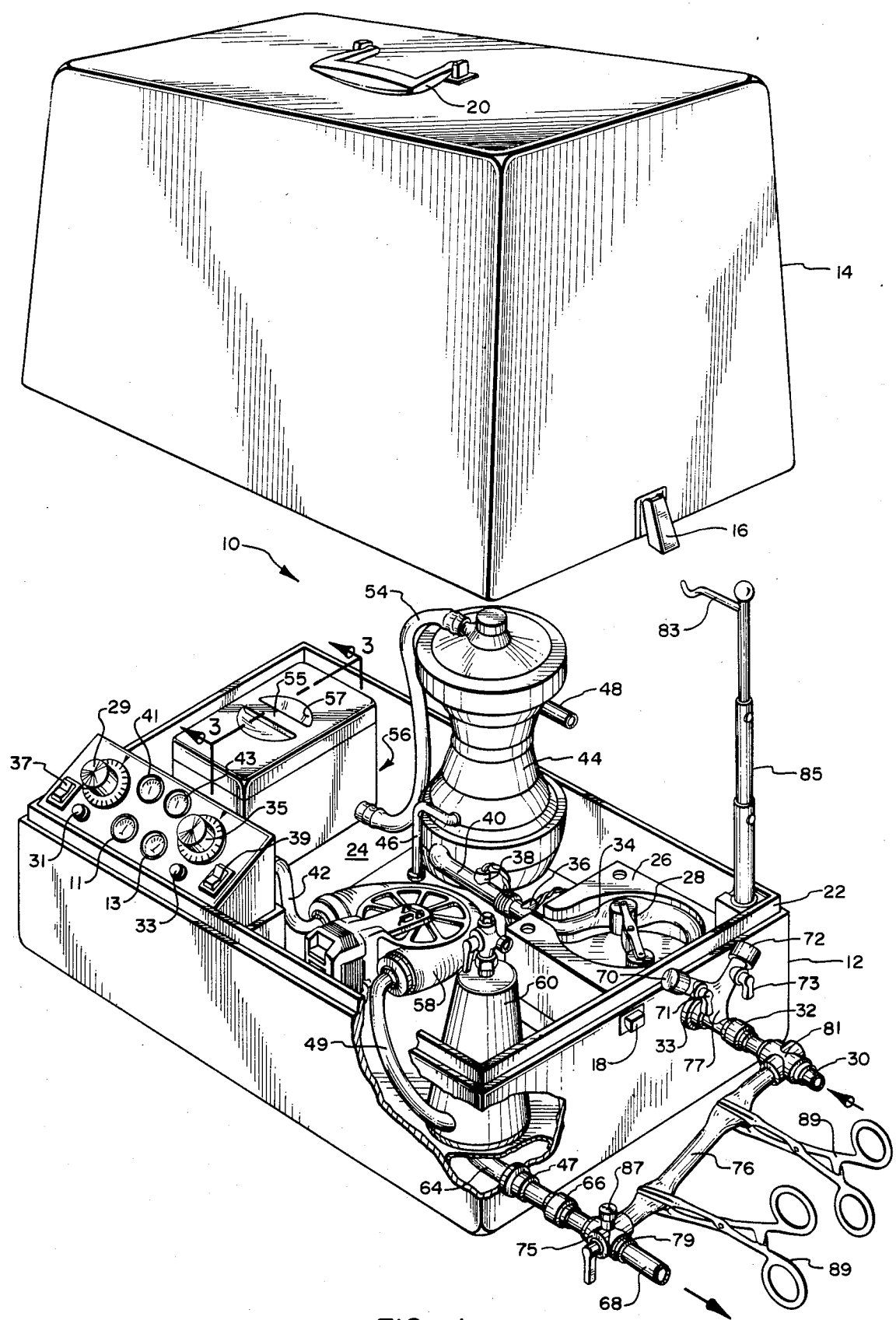
FIG. 1 is a perspective view which schematically illustrates one presently preferred embodiment of the mechanical heart-lung substitution system of the present invention mounted in a portable carrying case.

Reference is first made to FIG. 1, which schematically illustrates a perspective view of one presently preferred embodiment of the invention. As illustrated in FIG. 1, the heart-lung substitution system generally designated at 10 is mounted within a portable carrying case which comprises a bottom part 12 and a top cover 14. The cover 14 is adapted to be securely connected to the bottom part 12 of the carrying case by means of the latch 16 which snaps over a corresponding hook 18. The bottom part 12 of the carrying case also is provided with a small ridge 22 which runs around the top periphery of the bottom part 12 of the carrying case so that the cover 14 will fit securely onto the bottom part 12. The top cover 14 is also provided with a handle 20 so that the entire system can be hand-carried.

Figure 2:
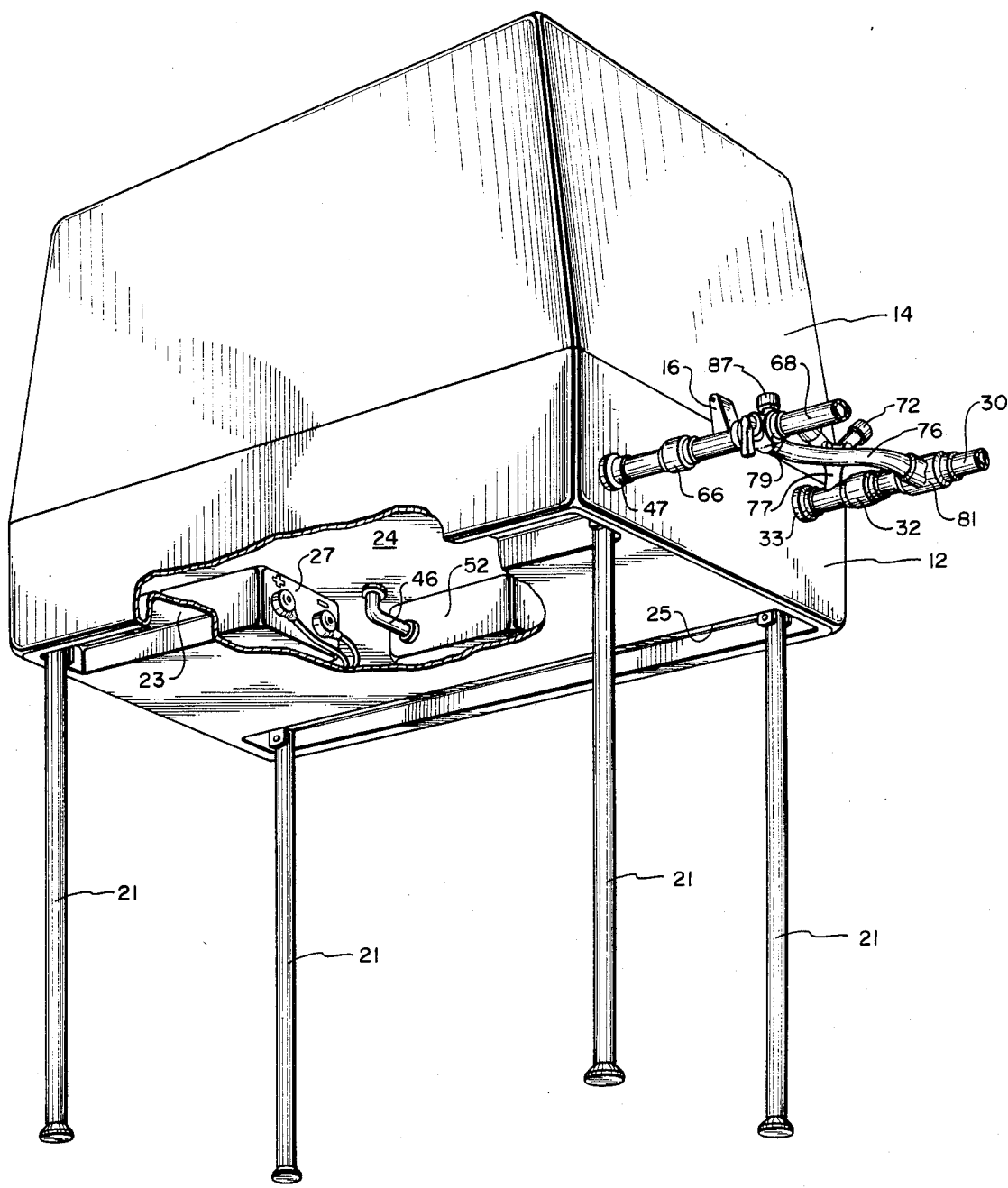
FIG. 2 is a perspective illustration showing the underside of the portable carrying case, with a portion broken away to reveal the battery and oxygen tank used in the present invention.

As shown in FIG. 2, the bottom 12 may also be provided with folding legs 21 which may be folded up to fit into channels 23 and 25 formed on the underside of bottom part 12. Thus, the carrying case can be either supported by placing it upon the ground or a table, or by elevating it if need be by unfolding the legs 21. This helps to increase the versatility of the mechanical heart-lung system 10.

Figure 4:
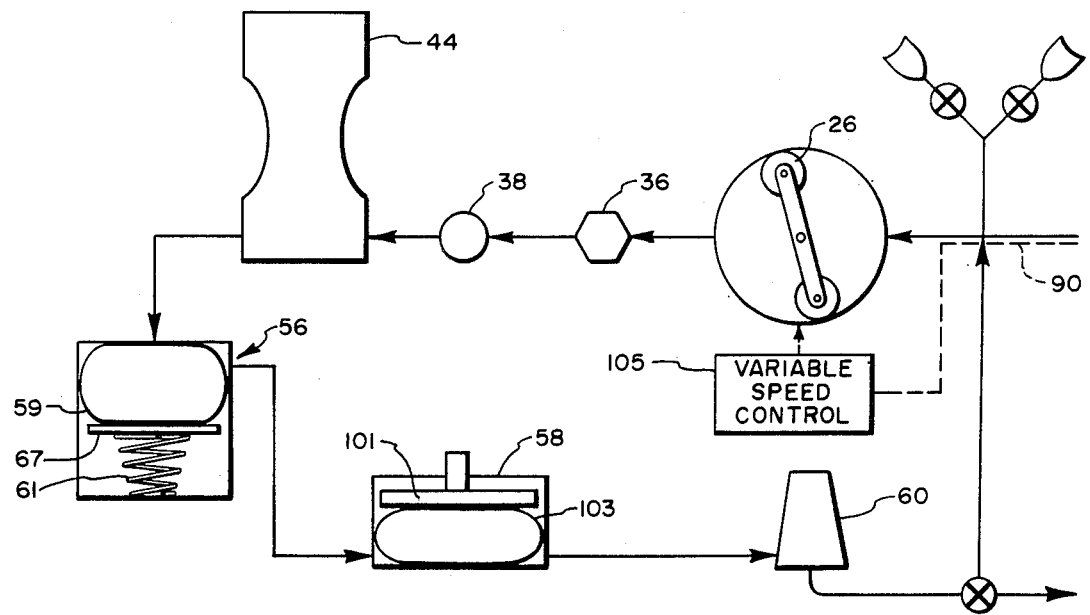
FIG. 4 is a schematic flow diagram illustrating the functional components of the system as used according to the method of the present invention.

With reference again to FIG. 1, the bottom part 12 of the carrying case is also provided with a platform 24 securely mounted inside the bottom part 12 of the carrying case. Mounted on the platform 24 is a right heart pump 26 which is comprised of a conventional roller pump having rollers 28 which pump the blood through tubing 34 as hereinafter more fully described. Tubing 34 runs through the end of the lower part 12 of carrying case and is secured by a fitting 33. Tubing 34 is also joined by another fitting 32 to another length of tubing 30 which, as hereinafter more fully described in connection with FIG. 4, is attached to a venous cannula for insertion into the vena caval system of the patient. Thus, as roller pump 26 is operated, blood is pumped by means of the venous cannula out of the vena caval system of the patient.

At the output of roller pump 26, the venous blood pumped out of the patient flows through a flow meter 36 and a pressure gauge 38 which are in line with tubing 40 attached at the output of pump 26. Flow meter 36 may be used to detect the flow rate of blood being pumped out of the patient and the pressure gauge 38 detects the hydraulic pressure at which the blood is flowing through tubing 40.

The blood next flows into a membrane blood oxygenator 44. Oxygenator 44 is attached through tubing 46 to a pressurized tank 52 (see FIG. 2) of oxygen-enriched gas. As shown in FIG. 2, the tank 52 of oxygen-enriched gas is stored beneath the platform 24. As the blood flows through the oxygenator 44, the blood is oxygenated and carbon dioxide is removed in accordance with well-known membrane gas exchange techniques and the oxygenated blood then flows through the blood outlet tube 54 to a compliant reservoir generally designated at 56. Gases are expelled by oxygenator 44 through a gas outlet 48. As used herein, the term "oxygenation" means blood gas exchange including removal of carbon dioxide as well as adding oxygen to the blood.

Figure 3:
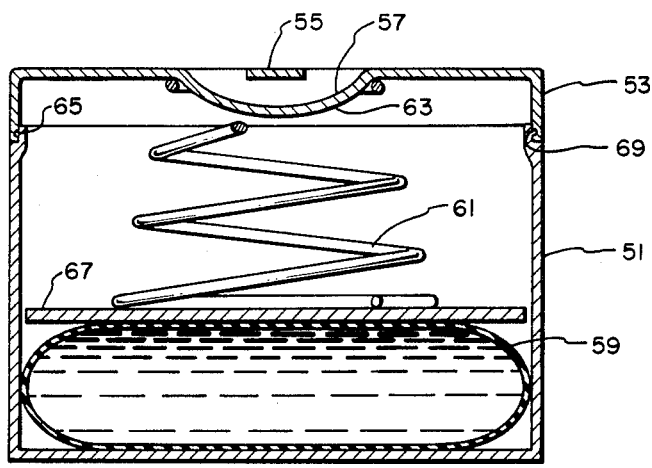
FIG. 3 is a cross-sectional view taken along line 3—3 of FIG. 1 so as to illustrate the compliance reservoir of the present invention in more detail.

With reference to FIG. 3, the compliant reservoir 56 comprises an outer case consisting of a bottom part 51 and a top cover 53 which snaps onto the bottom 51 by means of a small lip 65 provided at the upper edge of bottom 51 and a corresponding groove 69 formed in the edge of cover 53. Cover 53 is provided with a handle 55 accessible by means of an indentation 57 formed around the handle 55 (see also FIG. 1). Inside the reservoir, a compliant sac 59 of blood-compatible polymer receives blood from the tubing 54 connected to oxygenator 44. As blood fills the compliant sac 59, the sac 59 exerts an upward force on plate 67 which is held by a spring mechanism 61 secured between cover 53 and plate 67. In this manner, an increasing volume of blood filling sac 59 will result in increasing fluid pressure within sac 59, which may be used to automatically control stroke volume of the left heart pump 58, as hereinafter more fully explained. Other means may be utilized to provide the compliant reservoir, as for example a compliant sac sealed within an airtight chamber.

Blood is pumped from reservoir 56 through tubing 42 by left heart pump 58. The output of pump 58 is connected through tubing 49 to a blood filter and bubble trap 60. The blood filter and bubble trap 60 removes any accumulated particulate and/or gas microemboli and/or macro collections of air from the blood before it is returned to the patient's arterial system. From the filter and bubble trap 60, the blood is returned through a length of tubing 64 which extends through the end of the lower portion 12 of the carrying case by means of fitting 47 and is attached through a second fitting 66 to an arterial line 68. As hereinafter more fully described, the arterial line 68 is connected to an arterial cannula which may be inserted into the left (or both left and right) carotid artery of the patient for return of the blood to the patient's arterial system.

The venous and arterial lines 30 and 68 may be connected by a recirculation line 76 connected at "T" fittings 81 and 79. A "Y" connector 77 is also connected to venous line 30 and is provided with transfusion ports 70 and 72 which are controlled by two-way stopcocks 71 and 73. Blood, plasma, or other infusion fluids may be suspended from the arm 83 of a telescopically collapsible IV stand 85 and connected to ports 70 and/or 72 if transfusion of blood is needed in cases where the patient has lost large amounts of blood. The "T" fitting 79 on arterial line 68 is provided with a stopcock 75 having a port 87 which may be used for sampling arterial blood, sensing arterial line pressure or administering fluids and/or medications into the patient's arterial system. Recirculation line 76 will be typically clamped closed using clamps 89 during perfusion of the patient. When recirculation line 76 is open and blood lines 30 and 68 are closed, the recirculation line 76 permits the system to run without including the patient in the circuit, as for example when priming the circuit.

With reference to FIG. 2, both the right heart pump 26 and the left heart pump 58 are powered by means of a direct current electrical power supply which may be, for example, battery 27. As more fully explained hereinafter, the speed of the right and left heart pumps 26 and 58 can be controlled manually using instrumentation provided with the portable system. For example, as shown in FIG. 1, knobs 29 and 35 can be used to vary the speed of the right and left heart pumps 26 and 58, respectively. Switches 37 and 39 are used to turn the pumps on and off and small lamps 31 and 33 are used to indicate that the pumps are powered and ready for operation. Gauges 11 and 13 indicate flow rate and pressure detected at flow meter 36 and pressure gauge 38, respectively. If desired, gauges 41 and 43 can also be supplied to indicate the speed at which each pump is operating. However, as more fully explained below the mechanical heart-lung substitution system 10 of this invention is designed so as to be semi-automatic in its operation, thereby eliminating the need for manual control to a large extent.

Figure 5:
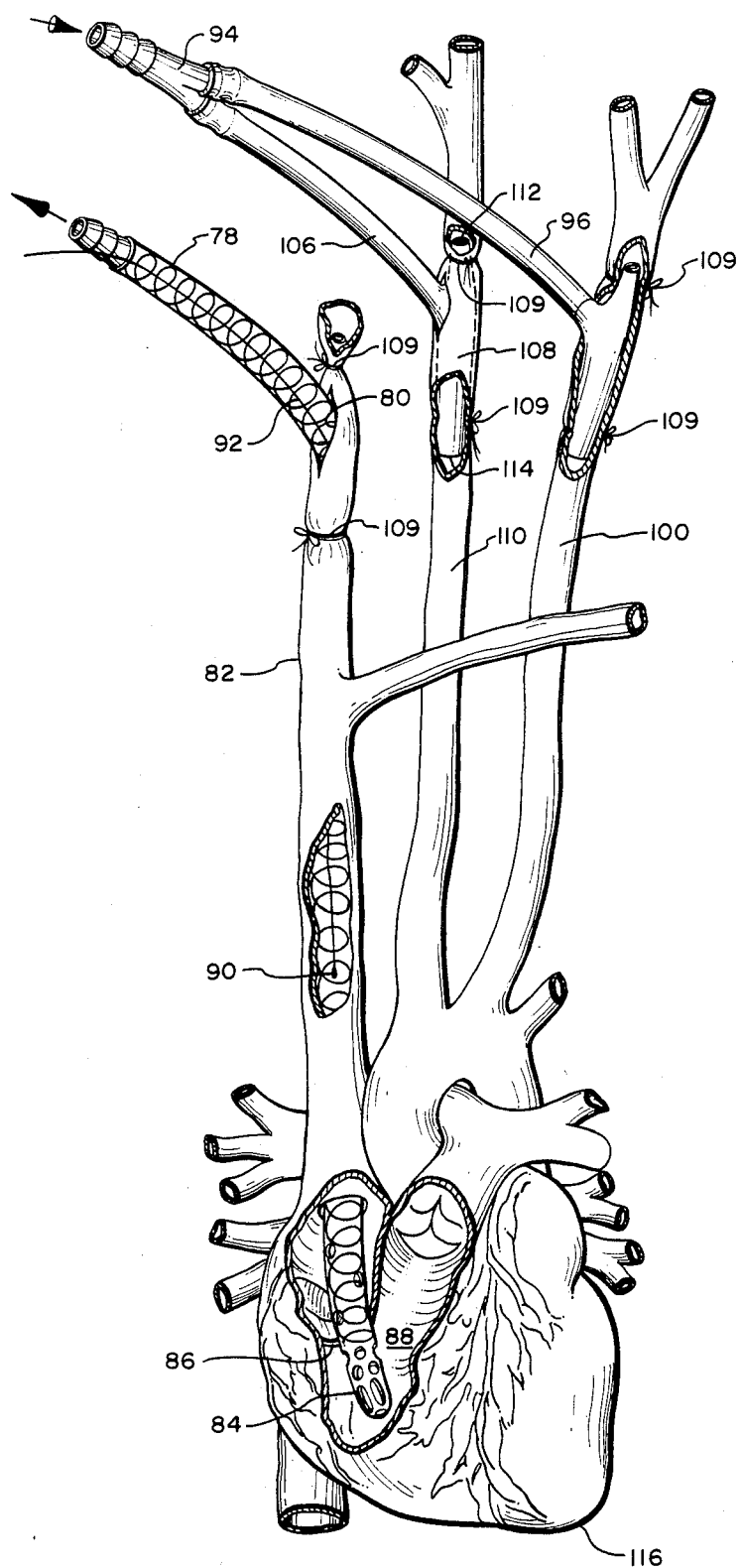
FIG. 5 is a perspective illustration shown in partial cross-section which schematically illustrates the manner in which the mechanical heart-lung substitution system is connected to the venous and arterial systems of a patient.

The method of operation of the system is best shown in FIGS. 4 and 5. Referring first to FIG. 5, the venous cannula 78 is a large-bore thin-walled bi-directional cannula which may be inserted under local anaesthesia through a small right cervical skin incision and through a second incision 80 in the right internal jugular vein of the patient. An arterial bi-directional cannula 106 is similarly inserted under local anaesthesia into the right common carotid artery of the patient utilizing the same skin incision made for the venous cannula insertion. As shown in FIG. 5, the tip 108 of the arterial cannula 106 has bi-directional blood outlets 112 and 114 at opposite ends thereof which permit the blood to be returned in both directions in the right common carotid artery 110. If higher blood flow rates at lower input pressures are desired, the left common carotid artery 100 may be similarly cannulated using a second bi-directional arterial cannula 96 which is essentially identical to arterial cannula 106. Both cannulae may be joined by a "Y" connection 94 which delivers blood to the patient from line 68 of the mechanical heart-lung substitution system. Each bi-directional cannula 78, 106 and 96 is tied off with ligatures 109 to prevent bleeding.

With continued reference to FIG. 5, the venous cannula 78 is inserted through the vena cava 82 of the patient until the perforated tip 84 of the long arm of the cannula extends through the tricuspid valve 86 of the right atrium of heart 116 into the right ventricle 88. As illustrated at 90, a small catheter-tip pressure transducer is attached at the outside wall which defines the lumen of the venous cannula 78. Transducer 90 is located on the outer surface of cannula 78, lying in the superior vena cava approximately 12 centimeters upstream from the perforated tip 84. The pressure transducer 90 is attached by a thin wire 92 running in the wall of cannula 78 along the length of the venous cannula 78 back to the right heart pump 26. Pressure sensor 90 is used to control the rate at which blood is pumped by right heart pump 26 from the patient into the mechanical heat-lung system.

The perfusion of blood from the patient's right heart and vena caval system through the mechanical heart-lung substitution system 10 and back to the patient's arterial system is preferably accomplished at a maximum flow rate which should be as near as possible to the normal systemic blood flow rate for the patient (i.e., approximately 80 milliliters of blood per kilogram body weight per minute).

The operation of the mechanical heart-lung system 10 is semi-automatic in that the output of the right heart pump 26 is automatically controlled, as is the output of left heart pump 58, although one or both pumps can also be manually controlled. Significantly, as hereinafter more fully explained, in the automatic mode the output of left heart pump 58 automatically returns the same volume of blood to the patient and at the same rate as is pumped from the patient's vena cava by right heart pump 26.

A pressure sensor 90 is embedded in the wall of the venous cannula 78 and will sense the venous pressure in the patient's caval system. The pressure is converted by transducer 90 into a corresponding electrical signal which is input to the variable voltage potentiometer circuit 105 (see FIG. 4) that controls the right heart pump 26 so that the speed of the pump will maintain a central venous pressure of approximately 0 to 2 mmHg. When the venous blood pressure in the caval system of the patient's system is higher than 2 mmHg, right heart pump 26 will speed up in proportion to the central venous pressure of the patient, and when the pressure is lower than 0 mmHg the right heart pump 26 will decrease in speed so as to maintain the venous presure within the 0–2 mmHg range. In this manner, the system automatically pumps as much blood as possible from the patient so as to maintain a blood flow rate close to normal without collapsing the patient's vena cava. At any time during perfusion, the system can be switched to a manual mode of operation using the control knobs 29 and/or 35.

With reference to FIG. 4, blood from the right heart pump 26 is oxygenated by oxygenator 44 and then collected in the compliant reservoir 56. Internal hemodynamics of the mechanical heart-lung substitution system are controlled automatically by means of the expansile compliant sac 59 and spring mechanism 61, in combination with the pulse rate of left heart pump 58. As blood fills the compliant sac 59 beyond its original volume, the increasing volume in the sac 59 compresses spring 61 by means of plate 67, thus increasing pressure in the compliant sac 59 commensurate with increasing blood volume within the sac. This pressure becomes the filling pressure into the bladder 103 of pulsatile flow left heart pump 58 during the first half or intake portion of the pumping cycle of pump 58, and the volume of blood expelled from reservoir 56 is proportional to the pressure exerted by spring 61. Pump 58 includes a solenoid-actuated pusher plate 101 which empties the bladder 103 of pump 58 during the second half or pumping stroke of each pumping cycle. The pulse rate of left heart pump 58 can be automatically controlled by an electrocardiogram hook-up to the patient, or manually using control knob 35. Thus, as the blood flow from the patient into the mechanical heart-lung system increases, the volume of blood in the compliant reservoir 56 increases and the stroke volume of the left heart pump 58 automatically increases, resulting in automatic regulation of blood flow into the patient's arterial system such that the volume and rate of blood returned to the patient's arterial system is equal to the volume and rate of blood flowing out of the patient's caval system and right heart.

As previously mentioned, any time during perfusion the manual mode of operation can be selected by using the knobs 29 and 35 to adjust the output of either the right heart pump 26 or left heart pump 58 to accommodate for observed changes in the hemodynamics of the patient. Changes in hemodynamics may be observed using the flow meter gauge 11 and/or pressure gauge 13 (see FIG. 1).

Referring again to FIGS. 1 and 2, if additional perfusion flow rate and/or volume are desired, perfusion of appropriate electrolyte solutions, blood or blood products may be accomplished by using the transfusion ports 70 and 72. Each transfusion port 70 and 72 is controlled by a stopcocks 71 and 73 as mentioned above.

It should of course be appreciated that the system and method as generally described above may be implemented in a variety of ways without departing from the spirit and essential characteristics of the present invention. For example, one presently preferred embodiment of the system and method of the invention may be implemented as follows:

EXAMPLE 1

The venous return cannula 78 may comprise a wire-reinforced large diameter bi-directional cannula approximately 40 centimeters in length such as that manufactured by USCI, a division of C. R. Bard, Inc. of Billerica, Mass., Model No. 008019. The arterial cannulae 106 and 96 may be of the type generally illustrated and described in U.S. Pat. No. 4,173,981, incorporated herein by reference, slightly modified for purposes of the present invention by reducing the length of the long arm of each cannula to approximately one-third of the length as described in the aforesaid patent. Both the venous and arterial cannulae and their connecting adaptors and tubing are surface treated to make them thrombo-resistant.

The right heart pump 26 may be a conventional roller pump such as a Sarns (TM) pump. The flow meter may be a Gould Statham flow probe sensor Model No. SP 7519-500-604, and the pressure gauge may be a Statham Gould Strain Gauge Model Number PB23-DB. The control circuit 105 may comprise any appropriate commercially available solid state variable voltage potentiometer coupled with a current amplifier. Oxygenator 44 may be a William Harvey Model HF-4000 hollow fiber membrane oxygenator manufactured by Bard Cardiopulmonary Division of C. R. Bard, Inc., Santa Ana, Calif. or a Bentley Model BOS-CM microporous oxyenator manufactured by American Bentley, a subsidiary of American Hospital Supply Corporation of Irvine, Calif. The left heart pump may comprise a modified model MK 22C electromagnetic energy convertor integrated with a model IIIA dual pusher plate sac blood pump manufactured by Novacor Medical Corporation of Palo Alto, Calif. The blood filter and bubble trap may be a model AF-1025 or AF-1040 arterial line filter manufactured by American Bentley, a subsidiary of American Hospital Corporation. Pressure sensor 90 may comprise a Millar model MPC-500 catheter-tip pressure sensor manufactured by Millar, Inc. of Houston, Tex.

The initial volume of the compliant sac 59 may be approximately 400 cc. The gas delivered to the membrane oxygenator 44 may be 100% oxygen or a mixture of 96% oxygen and 4% carbon dioxide. The flow rate of gas into the oxygenator will typically be about one to two times that of the blood flow rate through the oxygenator. The temperature of blood flowing through the oxygenator is not controlled, resulting in mild hypothermia during long perfusions, which is not considered undesirable for the intended application of the system of this invention. Blood tubing and other materials of the system are selected based on thrombogenicity characteristics so as to provide an overall system which can be used without systemic anticoagulation. However, if clotting is a problem in any given component of the presently preferred embodiment, it can be overcome by applying antithrombogenic surface coatings to the components of the system, or by administration of prostacyclin and/or platelet-sparing drugs.

The power supply in the above example may comprise a direct current 10 volt electrical system provided by a rechargeable battery which will supply adequate power for up to 8 hours of operation.

In summary, the system and method of the present invention are intended to provide a substantial advancement in the state of the art of cardiopulmonary bypass techniques in temporary emergency situations. The system and method of the present invention provide a fully portable, self-contained semi-automatic mechanical heart-lung substitution system and method. The system and method permit temporary emergency cardiopulmonary bypass without the use of general anaesthesia and without major surgery, and operation of the system is automatically controlled so that it can be used outside the hospital environment by emergency personnel. The semi-automatic operation permits the system to be used without the need for skilled perfusionists and highly technical invasive monitoring equipment, and yet with effective and reliable results.

The invention may be embodied in other forms without departing from the spirit or essential characteristics of the invention, and the presently preferred embodiment as illustrated and described herein is to be considered in all respects only as illustrative and not restrictive of the scope of the invention as set forth in the claims.

What is claimed and desired to be secured by United States Letters Patent is:

1. A fully portable mechanical heart-lung substitution system for automatically regulating the volume and rate of venous blood pumped from a patient and the volume and rate of oxygenated blood pumped back to said patient such that blood is returned to the patient at substantially the same flow rate and volume as the blood pumped from the patient, said system comprising:
   a venous cannula adapted for insertion into a vein of said patient, said venous cannula comprising means for sensing the venous blood pressure within said vein as blood is withdrawn through said venous cannula;

a first pump connectable to said venous cannula for pumping blood from said vein through said venous cannula, said first pump being connectable to said means for sensing venous blood pressure and comprising means for controlling the speed of said pump in response to said means for sensing said venous blood pressure within said vein such that the rate at which blood is pumped through said first cannula increases or decreases with a corresponding increase or decrease in said venous blood pressure;

means, connected to said first pump, for oxygenating the blood pumped from said vein;

reservoir means, connected to said means for oxygenating said blood, and comprising means for increasing the blood pressure within said reservoir means commensurate with increasing blood volume within said reservoir means, whereby said blood pressure within said reservoir means serves as a filling pressure for a second pump;

a second pump comprising means for providing pulsatile flow of oxygenated blood back to said patient, said second pump having a pump cycle comprised of an intake stroke and a pumping stroke, and said second pump being connected to said reservoir means and comprising means for receiving said blood expelled from said reservoir means during said intake stroke and comprising means for pumping said oxygenated blood received from said reservoir means during said pumping stroke, the filling pressure communicated to said second pump by said reservoir means thereby determining the volume of blood received by said second pump during each said intake stroke and the volume of blood pumped by said second pump during each said pumping stroke such that the volume and rate of blood returned to said patient is automatically controlled so as to be substantially the same as the volume and rate of blood pumped by said first pump;

means, connected to said second pump, for filtering said blood;

an arterial cannula connectable to said means for filtering said blood, said arterial cannula being adapted for insertion into an artery of said patient for return of said blood into said artery; and a carrying case adapted to be hand-carried, and means for mounting said first and second pumps, said reservoir means, said means for oxygenating said blood and said means for filtering said blood in said carrying case.

2. A system as defined in claim 1 wherein said venous cannula comprises a perforated tip adapted for insertion into the right ventricle of the heart of said patient, and said venous cannula having a length which is sufficient to permit insertion through the right internal jugular vein through said patient's vena caval system to said right ventricle.

3. A system as defined in claim 2 wherein said means for sensing said venous blood pressure within said vena caval system comprises a pressure sensor attached to the exterior wall of said venous cannula at a point upstream from said perforated tip of said cannula.

4. A system as defined in claim 1 wherein said means for sensing venous blood pressure comprises a pressure sensor attached to the exterior wall of said venous cannula, said pressure sensor being connected to said means for controlling the speed of said first pump by an electrically conductive wire attached between said pressure sensor and said speed control means, and said pressure sensor comprising means for transducing venous blood pressure sensed within said vein into a corresponding electrical signal which is used to control the speed of said first pump and which is input to said speed control means through said 5. A system as defined in claim 1 wherein said first pump comprises a direct current roller pump.

6. A system as defined in claim 1 wherein said means for oxygenating said blood comprises a membrane oxygenator and a source of oxygen enriched gas connected to said oxygenator.

7. A system as defined in claim 1 wherein said reservoir means comprises a compliant sac and wherein said means for increasing said fluid pressure within said reservoir means commensurate with increasing blood volume within said sac comprises a spring mechanism for exerting pressure on said compliant sac as the volume of blood in said compliant sac increases and expands said sac.

8. A system as defined in claim 1 wherein said second pump comprises a direct current solenoid-actuated pressure plate pump.

9. A system as defined in claim 1 wherein said means for filtering said blood comprises means for removing air bubbles from said blood.

10. A system as defined in claim 1 wherein said arterial cannula comprises first and second outlet ports adapted for bi-directional return of blood to said artery of said patient.

11. A system as defined in claim 10 further comprising an additional arterial cannula adapted for insertion into a second artery of said patient, both said arterial cannulae being connected through a "Y" adapter connectable to said second pump.

12. A system as defined in claim 1 further comprising a flow meter connected between said first pump and said means for oxygenating said blood.

13. A system as defined in claim 1 further comprising a pressure gauge connected between said first pump and said means for oxygenating said blood.

14. A system as defined in claim 1 further comprising first and second transfusion ports connected at the input of said first pump, said first and second inlet ports comprising valve means for controlling the opening and closing of said ports.

15. A system as defined in claim 14 further comprising valve means connected at the outlet of said second pump.

16. A system as defined in claim 15 further comprising a length of recirculation tubing interconnecting said valve means at the outlet of said second pump and said inlet of said first pump, and means for clamping said tubing so as to selectively open or close said length of recirculation tubing.

17. A system as defined in claim 1 further comprising means for manually adjusting the speed of said first and second pumps and means for visually indicating when said first and second pumps are in operation.

18. A system as defined in claim 1 wherein said carrying case comprises a bottom portion having a platform on which said first and second pumps, said reservoir means, said means for oxygenating said blood, and said means for filtering said blood are mounted, and a top portion for enclosing said system within said carrying case when said top and bottom portions are joined together.

19. A system as defined in claim 18 wherein said bottom portin comprises a plurality of foldable legs for supporting said bottom portion when said legs are unfolded.

20. A heart-lung substitution system comprising:
first cannula means adapted for insertion into a vein of a patient and comprising means for sensing venous blood pressure within said vein as blood is pumped through said first cannula means;
means for pumping blood from said vein through said first cannula means;
means for controlling the speed of said means for pumping blood from said vein such that the speed of said means for pumping blood is automatically increased as said venous blood pressure increases and said speed is automatically decreased as said venous blood pressure decreases;
means for oxygenating said blood;
means for pumping said oxygenated blood back to said patient;
reservoir means, connected between said means for oxygenating said blood and said means for pumping said oxygenated blood back to said patient, and comprising means for increasing the blood pressure within said reservoir means commensurate with increasing blood volume within said reservoir means, whereby said blood pressure within said reservoir means serves as a filling pressure for said means for pumping said oxygenated blood back to said patient; and
second cannula means for insertion into an artery of said patient for returning said oxygenated blood to said artery of said patient.

21. A system as defined in claim 20 wherein said first cannula means comprises an outer wall which defines a lumen therethrough, and wherein said means for sensing said venous blood pressure is attached to said outer wall so as to be positioned inside said vein but outside said lumen after insertion of said first cannular into said vein.

22. A system as defined in claim 21 wherein said means for sensing said venous blood pressure comprises a pressure sensor for converting said venous blood pressure to an electrical signal proportional in magnitude to said venous blood pressure sensed within said vein.

23. A system as defined in claim 22 wherein said means for sensing said venous blood pressure further comprises an electrical conductor attached to said outer wall of said cannula and connected between said pressure sensor and said means for pumping blood from said vein.

24. A system as defined in claim 20 wherein said reservoir means comprises a compliant sac having an inlet and an outlet and wherein said blood pressure increasing means comprises a spring mechanism for exerting pressure on said sac, said inlet being connected to said means for oxygenating said blood, and said compliant sac being adapted to resiliently expand in volume to accommodate increasing blood volume within said sac as blood is collected therein.

25. A system as defined in claim 24 wherein said outlet of said compliant sac is connected to said means for pumping said oxygenated blood back to said patient, such that the volume and rate of oxygenated blood pumped back to said patient is automatically controlled so as to be substantially the same as the volume and rate of blood pumped out of said patient's vein.

26. A system as defined in claim 20 further comprising means for measuring the rate of flow of said blood from said means for pumping blood from said vein.

27. A system as defined in claim 20 further comprising means for measuring blood pressure of blood pumped by said means for pumping blood from said vein.

28. A system as defined in claim 20 further comprising means for manually controlling the speed of each said means for pumping said blood.

29. A system as defined in claim 20 further comprising means for filtering said blood before it is returned to said artery of said patient.

30. A system as defined in claim 20 further comprising means for recirculating said blood back through said system without pumping additional blood from said vein and without returning blood to said artery of said patient.

31. A system as defined in claim 20 further comprising means for hand-carrying said system in a self-contained carrying case.

32. A method for pumping venous blood from a vein of a patient and for pumping oxygenated blood back to an artery of said patient, comprising the steps of:
inserting a first cannula into said vein of said patient and inserting a second cannula into said artery of the patient;
pumping blood from said vein through said first cannula;
sensing blood pressure within said vein as blood is pumped through said first cannula;
controlling the rate at which blood is pumped through said first cannula such that said rate is automatically increased as said blood pressure increases and said rate is automatically decreased as said blood pressure decreases;
oxygenating said blood after it is pumped through said first cannula;
collecting said oxygenated blood in a reservoir, said reservoir comprising means for increasing the blood pressure within said reservoir commensurate with increasing blood volume within said reservoir;
filling a blood pump with oxygenated blood from said reservoir and pumping said oxygenated blood back to said artery of the patient through said second cannula, said blood pressure within said reservoir serving as a filling pressure for said blood pump whereby the filling pressure communicated to said blood pump by said reservoir determines the volume of blood received by said blood pump and pumped by said blood pump back to said artery of the patient.

33. A method as defined in claim 32 wherein said step of inserting said first cannula comprises inserting said first cannula through said patient's vena cava to a point within the right ventricle of said patient's heart.

34. A method as defined in claim 32 wherein said step of inserting said second cannula comprises inserting said second cannula into the left common carotid artery of said patient.

35. A method as defined in claim 34 further comprising the step of inserting a third cannula in the right common carotid artery of said patient.

36. A method as defined in claim 32 wherein said second cannula is bi-directional.

37. A method as defined in claim 32 wherein said step of pumping blood from said vein comprises pumping blood from said vein at a rate of approximately 80 milliliters per kilogram of body weight per minute.

38. A method as defined in claim 32 wherein said step of sensing venous blood pressure within said vein comprises the step of attaching a catheter-tip pressure transducer to said first cannula such that said pressure transducer is positioned inside said vein when said cannula is inserted therein.

39. A method as defined in claim 32 wherein said step of controlling the rate at which blood is pumped through said first cannula comprises controlling said rate such that said blood pressure within said vein is automatically maintained at approximately 0 to 2 mmHg.

40. A method as defined in claim 32 wherein the reservoir comprises a compliant sac and wherein blood pressure within said sac increases with increasing blood volume within said sac.

41. A method as defined in claim 40 wherein the rate at which blood is pumped back to said patient is the same as the rate at which said blood fills said compliant sac.

42. A method as defined in claim 32 further comprising the step of filtering said blood after it is oxygenated.

43. A method as defined in claim 32 further comprising the step of measuring the rate of flow and blood pressure of said blood after it is pumped through said first cannula.

44. A method as defined in claim 32 wherein said blood is oxygenated in an oxygenator and wherein the method further comprises the steps of:
  clamping said first and second cannulae so as to prevent blood flow from or to said patient; and
  recirculating the oxygenated blood through said oxygenator without returning said blood to said patient.

45. In a heart-lung substitution system comprising a first cannula connected to the inlet of a first pump, a second cannula connected to the outlet of a second pump, an oxygenator connected at its inlet to the outlet of said first pump, and a reservoir connected between the outlet of said oxygenator and the inlet of said second pump, a method for providing extracorporeal oxygenation of a patient's blood comprising the steps of:
  inserting said first cannula into a vein of said patient and inserting said second cannula into an artery of said patient;
  operating said first pump so as to pump blood from said vein through said first cannula to said oxygenator;
  providing a pressure transducer attached to said first cannula such that said transducer is positioned within said vein when said first cannula is inserted therein;
  sensing venous blood pressure within said vein and automatically controlling said first pump so that the rate at which blood is pumped through said first cannula increases or decreases with a corresponding increase or decrease in said venous blood pressure;
  oxygenating said blood as it flows through said oxygenator from said first pump;
  collecting blood in said reservoir after said blood leaves said oxygenator, said reservoir comprising means for increasing blood pressure within said reservoir commensurate with increasing blood volume within said reservoir; and
  filling said second pump with oxygenated blood from said reservoir and operating said second pump so as to pump blood received from said reservoir back to said patient through said second cannula, said blood pressure within said reservoir serving as a filling pressure for said second pump whereby the filling pressure communicated to said second pump by said reservoir determines the volume of blood received by said second pump and pumped by said second pump back to said patient.

46. A method as defined in claim 45 wherein said heart-lung substitution system further comprises a flow meter and a pressure gauge connected to the outlet of said first pump and wherein said method further comprises the steps of measuring the rate of blood flow out of said first pump and measuring the blood pressure as said blood flows out of said first pump.

47. A method as defined in claim 45 wherein said heart-lung substitution system further comprises a hand-portable carrying case and means for mounting said first and second pumps, said oxygenator said reservoir and said first and second cannulae within said carrying case such that said system is self-contained and can be used outside the environment of a hospital facility.

48. A method as defined in claim 45 wherein said step of inserting said first cannula comprises inserting said first cannula through said patient's vena cava to a point within the right ventricle of said patient's heart.

49. A method as defined in claim 45 wherein said step of inserting said second cannula comprises inserting said second cannula into the left common carotid artery of said patient and wherein said method further comprises the step of inserting a third cannula into the right common carotid artery of said patient.

50. A method as defined in claim 49 wherein said second and third cannulae are each bi-directional.

51. A method as defined in claim 45 wherein said step of automatically controlling said first pump comprises controlling the rate at which said blood is pumped through said first cannula so as to maintain a venous pressure of from 0 to 2 mmHg.

52. A method as defined in claim 45 wherein said oxygenator comprises a membrane oxygenator.

53. A method as defined in claim 45 wherein said means for increasing blood pressure within said reservoir commensurate with increasing blood volume within said reservoir comprises a compliant sac for receiving blood from said oxygenator and a spring mechanism for exerting pressure on said compliant sac as the volume of blood within said sac increases.

54. A method as defined in claim 45 wherein said heart-lung substitution system further comprises means for filtering said blood after said blood leaves said reservoir and wherein said method further comprises the step of filtering said blood prior to pumping said blood back through said second cannula.

55. A method as defined in claim 45 wherein said heart-lung substitution system further comprises means for recirculating blood from said second pump to said first pump and wherein said method further comprises the steps of clamping said first and second cannulae so as to prevent blood flow from or to said patient and recirculating blood from said second pump back to said first pump without returning said blood to said patient.

56. A heart-lung substitution system comprising:

first cannula means adapted for insertion into a vein of a patient and comprising means for sensing venous blood pressure within said vein as blood is pumped through said first cannula means;

means for pumping blood from said vein through said first cannula means;

means for controlling the speed of said means for pumping blood from said vein such that the speed of said means for pumping blood is automatically increased as said venous blood pressure increases and said speed is automatically decreased as said venous blood pressure decreases;

means for oxygenating said blood;

means for pumping said oxygenated blood back to said patient comprising a solenoid-actuated pressure plate pump; and second cannula means for insertion into an artery of said patient for returning said oxygenated blood to said artery of said patient.

57. A heart-lung substitution system comprising:

first cannula means adapted for insertion into a vein of a patient and comprising means for sensing venous blood pressure within said vein as blood is pumped through said first cannula means;

means for pumping blood from said vein through said first cannula means;

means for automatically controlling the speed of said means for pumping blood from said vein and for automatically controlling the amount of blood pumped from said vein such that the speed of said means for pumping blood is automatically increased as said venous blood pressure within said vein increases and said speed is automatically decreased as said venous blood pressure within said vein decreases, thereby avoiding the collapse of said vein;

means for oxygenating said blood, and means for pumping said oxygenated blood back to said patient; and second cannula means for insertion into an artery of said patient for returning said oxygenated blood to said artery of said patient.

58. A system as defined in claim 57 further comprising reservoir means, connected between said means for oxygenating said blood and said means for pumping said oxygenated blood back to said patient, and comprising means for increasing the blood pressure within said reservoir means commensurate with increasing blood volume within said reservoir means, whereby said blood pressure within said reservoir means serves as a filling pressure for said means for pumping said oxygenated blood back to said patient.

59. A system as defined in claim 58 wherein said reservoir means comprises a compliant sac having an inlet and an outlet and wherein said blood pressure increasing means comprises a spring mechanism for exerting pressure on said sac, said inlet being connected to said means for oxygenating said blood, and said compliant sac being adapted to resiliently expand in volume to accommodate increasing blood volume within said sac as blood is collected therein.

60. A system as defined in claim 59 wherein said outlet of said compliant sac is connected to said means for pumping said oxygenated blood back to said patient, such that the volume and rate of oxygenated blood pumped back to said patient is automatically controlled so as to be substantially the same as the volume and rate of blood pumped out of said patient's vein.

61. A system as defined in claim 57 wherein said first cannula means comprises an outer wall which defines a lumen therethrough, and wherein said means for sensing said venous blood pressure is attached to said outer wall so as to be positioned inside said vein but outside said lumen after insertion of said first cannula into said vein.

62. A system as defined in claim 61 wherein said means for sensing said venous blood pressure comprises a pressure sensor for converting said venous blood pressure to an electrical signal proportional in magnitude to said venous blood pressure sensed within said vein.

63. A system as defined in claim 62 wherein said means for sensing said venous blood pressure further comprises an electrical conductor attached to said outer wall of said cannula and connected between said pressure sensor and said means for pumping blood from said vein.

64. A method for pumping venous blood from a vein of a patient and for pumping oxygenated blood back to an artery of said patient, comprising the steps of:

inserting a first cannula into said vein of said patient and inserting a second cannula into said artery of the patient;

pumping blood from said vein through said first cannula;

sensing blood pressure within said vein as blood is pumped through said first cannula;

automatically controlling the rate at which blood is pumped through said first cannula such that said rate is automatically increased as said blood pressure within said vein increases and said rate is automatically decreased as said blood pressure within said vein decreases, thereby avoiding collapse of said vein;

oxygenating said blood after it is pumped through said first cannula; and pumping said blood back to said artery of the patient through said second cannula after said blood is oxygenated.

65. A method as defined in claim 64 further comprising the step of:

collecting said oxygenated blood in a reservoir before pumping said oxygenated blood back to said artery, said reservoir comprising means for increasing the blood pressure within said reservoir commensurate with increasing blood volume within said reservoir; and wherein said oxygenated blood is pumped back to said artery by filling a blood pump with oxygenated blood from said reservoir and pumping said oxygenated blood back to said artery of the patient through said second cannula, said blood pressure within said reservoir serving as a filling pressure for said blood pump whereby the filling pressure communicated to said blood pump by said reservoir determines the volume of blood received by said blood pump and pumped by said blood pump back to said artery of the patient.

66. A method as defined in claim 65 wherein the reservoir comprises a compliant sac and wherein blood pressure within said sac increases with increasing blood volume within said sac.

67. A method as defined in claim 64 wherein said step of sensing venous blood pressure within said vein comprises the step of attaching a catheter-tip pressure transducer to said first cannula such that said pressure transducer is positioned inside said vein when said cannula is inserted therein.

* * * * *

UNITED STATES PATENT AND TRADEMARK OFFICE
CERTIFICATE OF CORRECTION

PATENT NO. : 4,610,656
DATED : September 9, 1986
INVENTOR(S) : J. D. Mortensen

It is certified that error appears in the above-identified patent and that said Letters Patent are hereby corrected as shown below:

Column 1, lines 15-16, "lift-threatening" should be --life-threatening--
Column 2, line 35, "so as to created" should be --so as to create--
Column 4, lines 3-4, "carrying case" should be --the carrying case--
Column 6, line 1, "long arm" should be --long arm 85--
Column 6, lines 14-15, "heat-lung system" should be --heart-lung system--
Column 6, line 47, "presure" should be --pressure--
Column 7, line 32, "a stopcocks" should be --stopcocks--
Column 10, line 10, "through said" should be --through said electrically conductive wire.--
Column 11, line 5, "portin" should be --portion--

Signed and Sealed this

Fourteenth Day of April, 1987

Attest:

DONALD J. QUIGG

Attesting Officer

Commissioner of Patents and Trademarks